United States Patent
Shum et al.

(10) Patent No.: US 9,707,183 B2
(45) Date of Patent: Jul. 18, 2017

(54) OSMOTIC DRYING OF ALL-AQUEOUS EMULSIONS

(71) Applicant: VERSITECH LIMITED, Hong Kong (CN)

(72) Inventors: Ho Cheung Shum, Hong Kong (CN); Qingming Ma, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 0 days.

(21) Appl. No.: 14/722,505

(22) Filed: May 27, 2015

(65) Prior Publication Data
US 2015/0342891 A1    Dec. 3, 2015

Related U.S. Application Data

(60) Provisional application No. 62/003,357, filed on May 27, 2014.

(51) Int. Cl.
| | |
|---|---|
| *A61K 9/48* | (2006.01) |
| *A61J 3/07* | (2006.01) |
| *A61K 35/13* | (2015.01) |
| *A61K 38/43* | (2006.01) |
| *A61K 9/16* | (2006.01) |
| *C12N 5/00* | (2006.01) |

(52) U.S. Cl.
CPC .............. *A61K 9/4833* (2013.01); *A61J 3/07* (2013.01); *A61K 9/1652* (2013.01); *A61K 35/13* (2013.01); *A61K 38/43* (2013.01); *C12N 5/0012* (2013.01); *C12N 2533/70* (2013.01); *C12N 2533/72* (2013.01)

(58) Field of Classification Search
CPC .... A61K 9/4833; A61K 9/1652; A61K 35/13; A61K 38/43; A61J 3/07; C12N 5/0012; C12N 2533/70; C12N 2533/72
See application file for complete search history.

(56) References Cited

U.S. PATENT DOCUMENTS

2008/0125552 A1* 5/2008 Schocker et al. ........ B01J 13/20
525/452

OTHER PUBLICATIONS

Bing-Zheng Lia, Li-Jun Wangb, Dong Lia, Bhesh Bhandaric, Shu-Jun Lid, Yubin Lane, Xiao Dong Chena, f, Zhi-Huai Maoa, "Fabrication of starch-based microparticles by an emulsification-crosslinking method", Journal of Food Engineering vol. 92, Issue 3, Jun. 2009, pp. 250-254.
Lixiong Wen, Kyriakos D. Papadopoulos, "Effects of Osmotic Pressure on Water Transport in W1/O/W2 Emulsions", Journal of Colloid and Interface Science, vol. 235, Issue 2, Mar. 15, 2001, pp. 398-404.
María Chávarri, Izaskun Marañón and María Carmen Villarán, "Encapsulation Technology to Protect Probiotic Bacteria", pp. 502-540, Oct. 3, 2012.
"Microspheres: Technologies and Global Markets", BBC Research, Jul. 2013 http://www.bccresearch.com/market-research/advanced-materials/microspheres-global-markets-avm073b.html.
Kaymak-Ertekin, M.Sultanoglu,Journal of Food Engineering, 46, pp. 243-250 (2000).
H. C. Shum, J. Varnell,D, A, Weitz, Biomicrofluidics, 6, p. 012808 (2012).
Z. Liu, H. C. Shum,Biomicrofluidics, 7, p. 0441178 (2013).
A. D. Diamond, J. T. Hsu, Biotechnology Techniques, vol. 3, No. 2, pp. 119-124 (1989).

* cited by examiner

*Primary Examiner* — Nathan M Nutter
(74) *Attorney, Agent, or Firm* — Leason Ellis LLP

(57) ABSTRACT

A one-step method for fabricating solidified particles from all-aqueous emulsion droplets involves solidification and drying of the droplets by osmosis. According to this method the fabrication of solidified particles is induced by implementing a high osmotic pressure gradient between the internal phase and external phase of the all-aqueous emulsion. The resultant extraction of water leads to solidification of the emulsion droplets. This approach provides mild conditions for encapsulating bioactive ingredients or other delicate components to conveniently fabricate bio- and cyto-compatible particles because it does not involve the introduction of external energy used in conventional drying. Such conventional external energy inputs are time-consuming, so the method is more efficient.

18 Claims, 5 Drawing Sheets

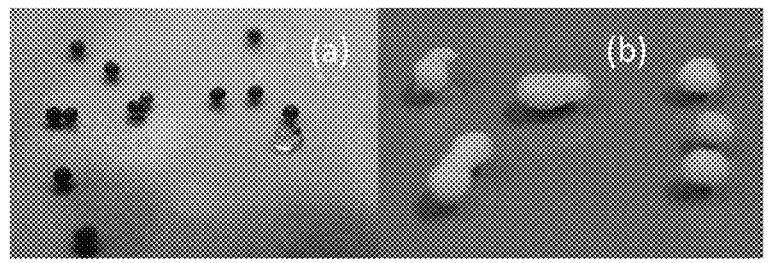
FIG. 3(a)   FIG. 3(b)
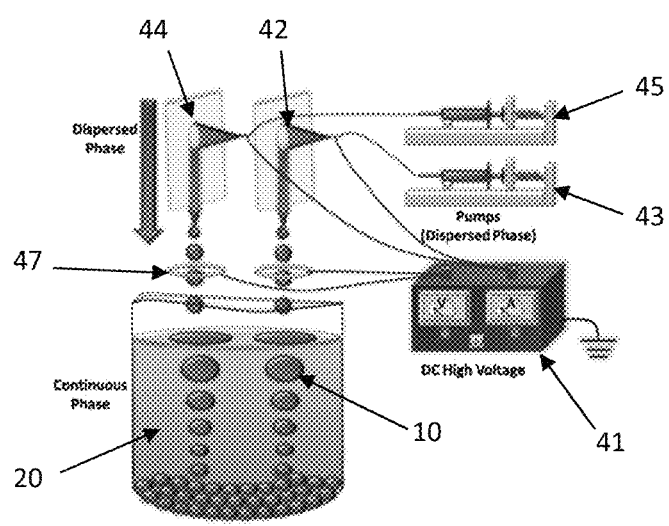
FIG. 4

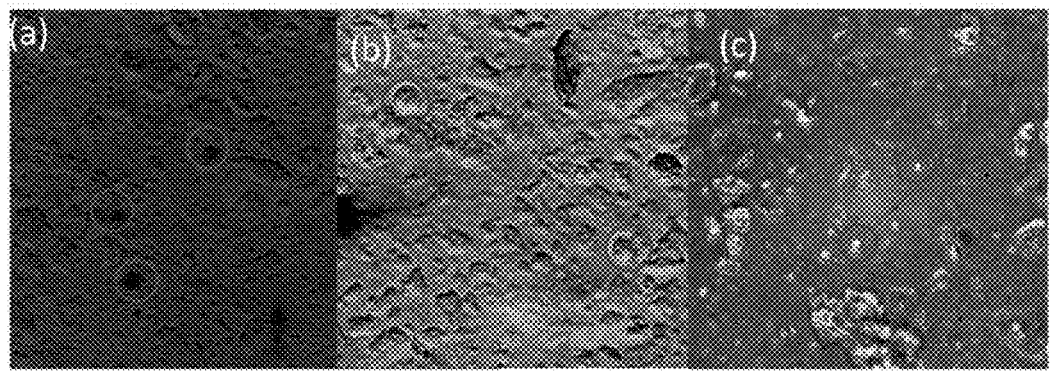
FIG. 6(a)      FIG. 6(b)      FIG. 6(c)
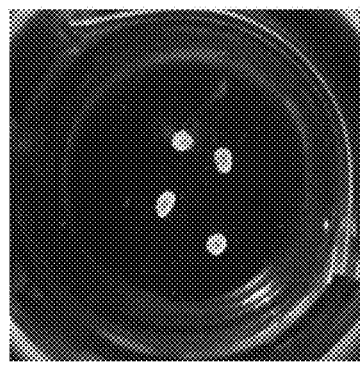 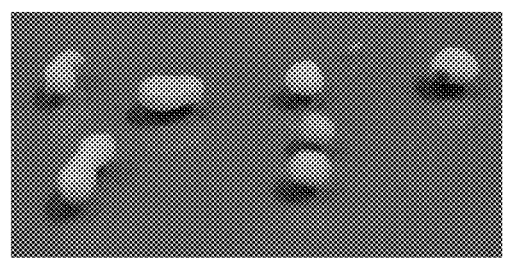
FIG. 7(a)      FIG. 7(b)
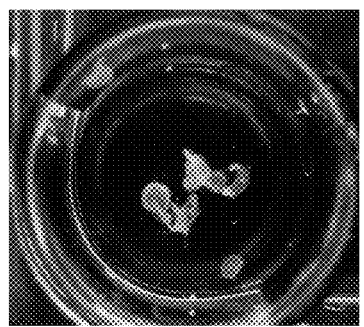 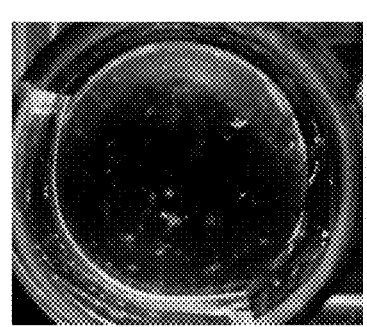
FIG. 8(a)      FIG. 8(b)

OSMOTIC DRYING OF ALL-AQUEOUS EMULSIONS

CROSS-REFERENCE TO RELATED APPLICATIONS

The present application claims priority to U.S. Provisional Application No. 62/003,357 filed May 27, 2014, which is incorporated herein in its entirety.

FIELD OF THE INVENTION

The present invention relates generally to a method for fabricating solidified particles or micro-particles based on an all-aqueous emulsion system containing two or more different immiscible aqueous phases with a high osmotic pressure gradient between them. More specifically, the method relies on osmosis-induced water extraction from the internal phase to the external phase by increasing the concentration of osmolytes in the external phase. This method can be applied to the fabrication of biocompatible solidified particles.

BACKGROUND OF THE INVENTION

As shown in FIG. 1 an emulsion consists of droplets of one internal phase 10 dispersed in a second immiscible fluid 20, called an external or continuous phase. Examples of common emulsions are oil-in-water and water-in-oil emulsions. The conversion of the droplets to solidified particles has significant commercial applications. Existing ways to convert emulsion droplets to solidified particles include the introduction of chemical crosslinking agents that trigger chemical reaction crosslinking and polymerization upon stimuli, such as optical illumination and UV crosslinking. Other ways include heating, vacuum drying and freeze drying for a certain period of time. All of these ways require intensive external energy inputs and additional subsequent steps.

Osmosis-induced water extraction, i.e., osmotic dehydration, is now widely used in different fields, such as food preparations, agricultural formulations, red blood substitutes, cosmetics and pharmaceuticals. In the food industry, water is extracted from objects like fruits and vegetables by immersing them in an aqueous solution with a high osmotic pressure due to the high concentration of sugars and salts in the solution. Water in vegetable tissues can be partially removed using this method and thus preservation of food can be achieved. Control of the osmotic-pressure-driven water migration between the two aqueous phases in an emulsion system has also been reported.

When used in the food industry, the conversion of liquid flavor materials into easy-to-handle solids can improve the stability and can control the release of dried active food ingredients, such as flavors, enzymes, etc. Besides, it also provides protection against degrading reactions and prevents the loss of flavor.

Moreover, osmotic dehydration is used as a pre-treatment prior to freezing, freeze drying, vacuum drying and air drying. Control of the osmotic-pressure-driven water migration between the two aqueous phases in water/oil/water (W/O/W) emulsions has been reported and the dynamic of water transportation has also been studied. The process is affected by lots of parameters such as the magnitude of the osmotic pressure gradients between the two aqueous phases, the nature and concentrations of the surfactants, and the nature and viscosity of the oil phase, etc.

As disclosed in Kaymak-Ertekin, M. Sultanoglu, *Journal of Food Engineering*, 46, 243-250 (2000), osmosis-induced water extraction from raw material, such as fruits and vegetables, is achieved by placing the solid/semi solid material, whole or in pieces, in a hypertonic solution (sugar and/or salt) with a simultaneous counter diffusion of solutes from the osmotic solution into the tissues. The article recommends this processing method as a way to obtain better quality food products. Partial extraction of water allows structural, nutritional, sensory and other functional properties of the raw material to be modified.

Using a classical microfluidic device with an applied electrical field, the generation of droplets between two immiscible aqueous phases can be tuned and controlled. A method based on electrospray has been proposed to generate water-in-water (w/w) droplets in controlled size and uniformity. The method utilizes the electrical field applied to the microfluidic device to help control the formation of droplets. See, Z. Liu, H. C. Shum, *Biomicrofluidics*, 7, 044117 (2013).

Within all-aqueous emulsion systems, a method has been proposed to generate droplets of controlled and uniform diameter with a good production rate. The introduction of a perturbation through a mechanical vibrator has been suggested to produce droplets with controlled size and uniformity. The method suggests a biologically and environmentally friendly platform for droplet microfluidics and establishes the potential of water-in-water (w/w) droplet microfluidics for encapsulation-related applications. H. C. Shum, J. Varnell, D. A. Weitz, *Biomicrofluidics*, 6, 012808 (2012)

The phase diagrams at 22° C. for aqueous two-phase systems composed of dextran and polyethylene glycol (PEG) solutions are determined in the article, A. D. Diamond, J. T. Hsu, *Biotechnology Techniques*, 3, 119-124 (1989). The effects of the molecular weight of PEG and dextran on phase separation are illustrated in the article.

Recent advances in the generation of particles based on emulsion systems have led to applications in various fields such as the food, cosmetics and drug delivery industries. When the preservation of the bioactivity of particles in the form of encapsulated delicate components is desired, the fabrication conditions as well as the process should be biocompatible. All-aqueous emulsions can be generated using the so-called aqueous two-phase systems (ATPS), which form two immiscible aqueous phases with attractive features, such as their biocompatibility or their non-toxicity. Thus, in the medical industry, micro-particles can be used as safe carriers for controlling the release of bioactive compounds.

Micro-particles made from all-aqueous emulsions have the potential to become one of the most promising and extensively used mediums for encapsulation due to their non-toxicity, storage stability, cost-effectiveness as well as the simplicity of the fabrication process. They can be fabricated by different kinds of methods, such as a spray drying method or a traditional homogenization methods. The latter one needs an additional step to solidify the emulsion droplets; one common way to do so is to introduce chemical crosslinking agents that trigger crosslinking and/or polymerization upon stimuli, including optical illumination. So far, there have been no reports concerning the osmotic drying of micro-particles in all-aqueous emulsion systems without further external energy or chemical inputs.

Micro-particles, like starch, gelatin and dextran microparticles, can be prepared by traditional homogenization crosslinking methods using additional chemicals as crosslinking agents. For example, in a previous study cross-linked gelatin microspheres with encapsulated bone morphogenetic protein 2 were fabricated by an emulsification process and stabilized by crosslinking with a small molecule with genipin as the crosslinking agent. To get the final solidified particles or microspheres after crosslinking, the microspheres need to be further incubated at −80° C. for 2 hours before being lyophilized. The whole process requires intensive external energy inputs and can be very time-consuming. See, L. Solorio, C. Zwolinski, A. W. Lund, M. J. Farrell, and J. P. Stegemann, *Journal of Tissue Engineering and Regenerative Medicine*, 4, 514-523 (2010)

Other emulsion-based methods always require additional steps, such as external agitation, heating, vacuum drying or freeze drying, for certain duration of time before fully dried micro-particles can be obtained. Moreover, these methods are all highly energy-intensive. In addition, other active ingredients, such as biological cells, tissues, drugs, DNA and leading compounds including proteins, for encapsulation in micro-particles require delicate handling for proper protection of their bioactivities and good preservation of their inherent properties Accordingly, it is desired to provide a generic method for one-step fabrication of solidified particles based on an all-aqueous emulsion containing two immiscible aqueous phases.

SUMMARY OF THE INVENTION

The present invention provides a method, based on the osmotic pressure gradient between the internal and external phases of an emulsion, for converting, e.g., drying, aqueous droplets of the internal phase into solidified particles. It is based on the osmotic pressure gradient between the internal and external phases, so it does not necessitate any alteration of the process of particle fabrication. It can be applied to fabricate solidified particles based on all-aqueous droplet microfluidics with high biocompatibility.

The osmotic pressure gradient between the internal and external phases of the emulsion can induce water extraction from the internal phase, thus inducing the solidification of the droplets into particles. By choosing components with different molecular weights in the external phase, the size and water content of the fabricated particles and the fabrication time can be tuned and controlled. The internal phase can include an inactive dissolved structural component, e.g., a starch, resulting in the formation of starch particles. Moreover, the internal phase can also include an active dissolved component, e.g., an enzyme, instead of or in addition to the structural component. The result will be either enzyme particles or starch particles encapsulating enzymes in the starch matrix.

The method of the present invention provides for the fabrication of solidified particles from all-aqueous emulsion systems containing different aqueous phases, without the necessity to execute subsequent crosslinking and solidifying steps. Therefore, the present invention allows for the one-step fabrication of solidified particles through classical droplet microfluidic approaches, where no external energy inputs are required. Thus, the invention can save time and energy. Further, as a result of its mild conditions and solidification processes, the present invention offers a biocompatible environment for application to the encapsulation of cells or other active biological ingredients located in the internal phase.

The fabrication of solidified particles based on an all-aqueous emulsion system containing two immiscible aqueous phases can be achieved by the introduction of osmosis induced water extraction from the internal phase to the external phase. The creation of an osmotic pressure gradient between the internal and external phases can be achieved by increasing the concentration of osmolyte in the external phase.

The external phase of the all-aqueous emulsion, which offers high osmosis, can be recycled, thus making the process cost-effective. The recycling of the external phase can occur after filtration and re-heating of the solution to restore the concentration of the osmolytes.

BRIEF DESCRIPTION OF THE DRAWINGS

The foregoing and other features of the present invention will be more readily apparent from the following detailed description and drawings of an illustrative embodiment of the invention in which:

FIGS. 3(a) and 3(b) are pictures of solidified starch particles (a) and dextran particles (b);

FIG. 4 is a schematic of a setup of apparatus according to the present invention;

FIGS. 6(a)-6(c) are optical microscope images of encapsulated cells released from solidified particles that are: (a) dead cells stained blue; (b) live cells not stained; and (c) live cells after encapsulation and subsequent release;

FIGS. 7(a) and 7(b) are illustrations of solidified dextran particles in PEG solution and dextran particles on a glass slide that were formed according to the present invention; and FIGS. 8(a) to 8(d) are illustrations of solidified chitosan particles in PEG solution, solidified CMS-Na particles in PEG solution, solidified corn starch particles in PEG solutions and solidified hydroxyethyl starch particles in PEG solution, respectively, formed according to the present invention.

DESCRIPTION OF AN ILLUSTRATIVE EXEMPLARY EMBODIMENT

Figure 1:
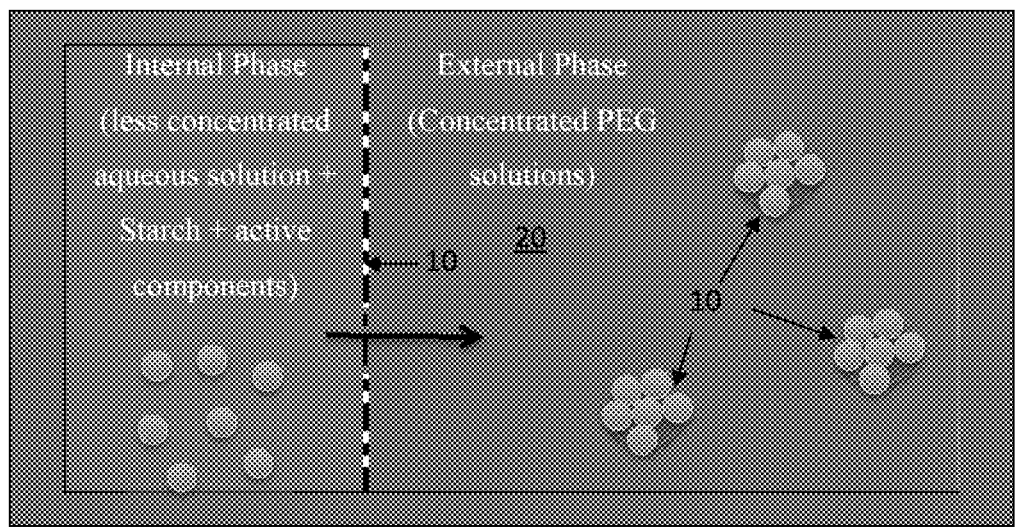
FIG. 1 is schematic diagram of an all-aqueous emulsion with internal and external phases.

The current invention is a method to solidify components in the internal phase of an all-aqueous emulsion (W/W) based on the principle of osmotic dehydration. In general, according to the method a concentrated solution (high osmolality), e.g. PEG or other macromolecules, is selected as the external phase of the all-aqueous emulsion system. Other aqueous solutions that induce phase separation with the external phase can be selected as the internal phase. For example, the internal phase can include components such as starch, which can induce phase separation and form structural components of the particle. The internal phase is then injected into the external phase, e.g., concentrated PEG solutions. Due to the osmotic pressure gradient between the internal and external phases, water is extracted from the internal phase to the external one, thereby concentrating the components in the internal phase to such an extent that solidification of the droplets into particles of the structural components is triggered.

If another component, for example an active ingredient such as an enzyme, is dissolved and mixed with the structural component in the internal phase, the active ingredient will be concentrated together with the structural components into the particles. As a result, the active component will be embedded within the matrix of the structural component, e.g. starch. Furthermore, if the active ingredient itself can behave as the structural component, the consequent particles will have active functions without any inert structural components. This approach to solidification of droplets does not require any further treatment and can achieve co-encapsulation of active ingredients in one step.

The current invention works for treating emulsion droplets made by different methods into solidified structures, such as particles with different structures. As water is gradually extracted from the starch droplets, starch is solidified during the process. In the end, the fully solidified starch particles can be collected easily, such as by filtration, for further applications. Moreover, the concentrated solution, e.g. PEG, can be recycled after the solidified objects have been taken out.

Glass capillary devices, which can be used for the generation of simple emulsions useful with the present invention, were previously developed at Harvard University in the group of D. A. Weitz. See U.S. Published Patent Application No. 2009/0131543 A1 of Weitz et al., which is incorporated herein in its entirety. Preferred examples of two phases fluids to generate simple water-in-water emulsions are Polysaccharide-Protein Systems (Dextran-gelatin; xanthan gum-whey protein; oxidized starch-gelatin; sodium alginate-sodium caseinate; gum arabic-gelatin; pectin-whey protein; pectin-casein; alginate-caseinate).

Preferred examples of combinations of two aqueous fluids to generate simple water-in-water emulsion are Polysaccharide-Polysaccharide Systems (dextran-dextran sulfate; dextran-hydroxypropyl dextran; fiscoll-dextran; dextran-polyvinyl alcohol; dextran-polyvinyl pyrrolidone; dextran-methylcellulose).

Preferred examples of combinations of two aqueous fluids to generate simple water-in-water emulsion are Polyethylene glycol (PEG)-based Systems (PEG-dextran; PEG-dextran HEMA; PEG-methyacrylated dextran; PEG-tripotassium phosphate; PEG-dextran sulfate; PEG-hydroxypropyl dextran; PEG-polyvinyl alcohol; PEG-polyvinyl pyrrolidone; PEG-methylcellulose). The generation of all-aqueous emulsions can be achieved by the use of any aqueous two phase system (ATPS) using the present method.

The introduction of an osmotic pressure gradient between the internal and external phases is achieved by increasing the concentration of osmolytes in the external phase in the emulsion system. The control of the size and water content of the solidified particles is achieved by choosing osmolytes with different molecular weights in the external phase. The drying rate can also be tuned by varying the molecular weights of the osmolytes in the external phase.

The biocompatibility of the fabricated particles is illustrated by encapsulating protein and cells in the internal phase and testing the bioactivity of the protein and the viability of cells.

EXAMPLES

According to the present invention, typically the internal phase is an aqueous solution of starch (MW=340, 10% wt.) and the external phase is an aqueous solution of polyethylene glycol (PEG, MW=8000, 40% wt.). The external phase has high osmolality, which is directly related to the concentration of the components. Then the internal phase is injected into the concentrated PEG solutions. Due to the osmotic pressure gradient between the internal and external phases, water is extracted from the internal phase to external one, thereby concentrating the components in the internal phase. Eventually the components are concentrated to such an extent that solidification is triggered. Thus, solidified starch particles can be obtained.

Figure 2:
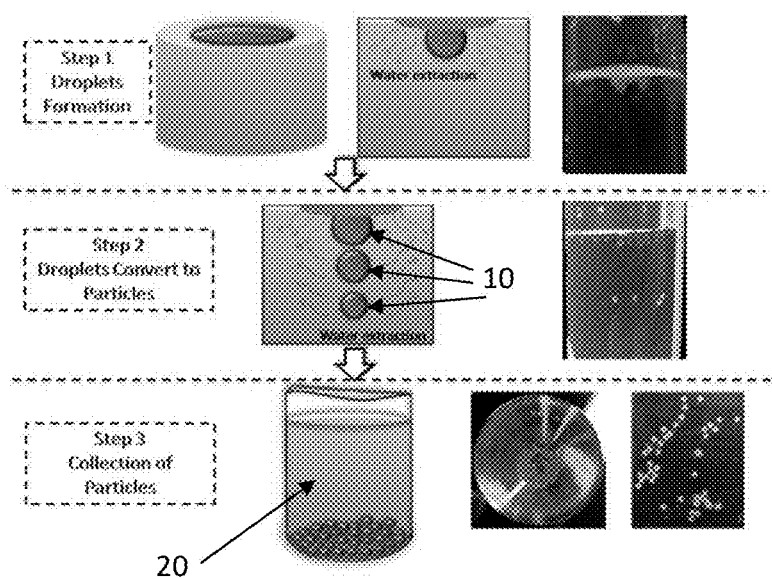
FIG. 2 is a schematic diagram of the droplets formation and solidification process.

The droplet formation and solidification process is shown in FIG. 2. This approach works for different water soluble materials. Dextran solution (T-500, MW=500 000, 15% wt.) is injected into the PEG solution (MW=300, 100%) and solidified dextran particles are fabricated. The colored starch particles and dextran particles are shown in FIG. 3.

Example 1

In Example 1 the internal phase is an aqueous solution of starch (MW=340, 10% wt.) and the external phase is an aqueous solution of polyethylene glycol (PEG, MW=8000, 40% wt.). The external phase has a higher osmosis, which is directly related to the concentration of the components. As illustrated in FIG. 2, the internal phase 10 is injected into the concentrated PEG solution 20. Due to the osmotic pressure gradient between the internal and external phases, water is extracted from the internal phase to the external phase, thereby concentrating the components in the internal phase. Eventually the concentration proceeds to such an extent that solidification is triggered. Thus, solidified starch particles are obtained. See FIG. 3(a).

Example 2

Using the apparatus setup of Example 1 (FIG. 2), the two immiscible phases are taken as polyethylene glycol (PEG, MW=300, 100% wt.) for the external phase and an aqueous solution of dextran (15% wt.) for the internal phase. The result is solidified dextran particles as shown in FIG. 3(b).

Example 3

In Example 3 the internal phase is an aqueous solution of starch (MW=340, 10% wt.) and the external phase is an aqueous solution of polyethylene glycol (PEG, MW=8000, 40% wt.). A microfluidic device as shown in FIG. 4 has one capillary tube 44 with an approximate tip diameter of 200 μm. A flexible tubing transports the internal fluid in the capillaries from an injector 45 at flow rates Qin determined by the injector. A direct current (DC) high voltage supply 41 is connected to the microfluidic platform as shown in FIG. 4 so as to create an electrical field between the capillaries and electrodes 47. The electrical field is controlled by changing the supplied voltage. By tuning the supplied voltage, the size of the emulsion droplets can be controlled as shown in FIG. 4.

Example 4

Figure 5A:
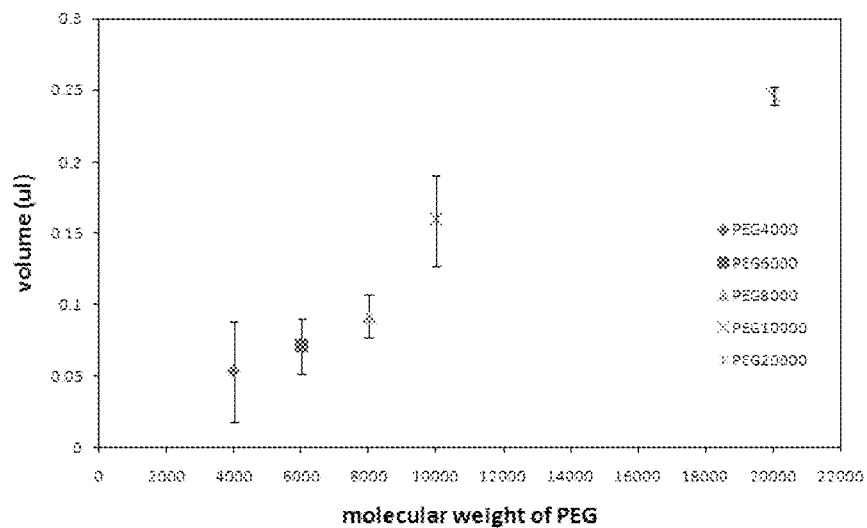
FIGS. 5(a)-5(c) are graphs showing the effects of different molecular weights of PEG on particles size (a), water content (b) and the entire fabrication time (c)
Figure 5B:
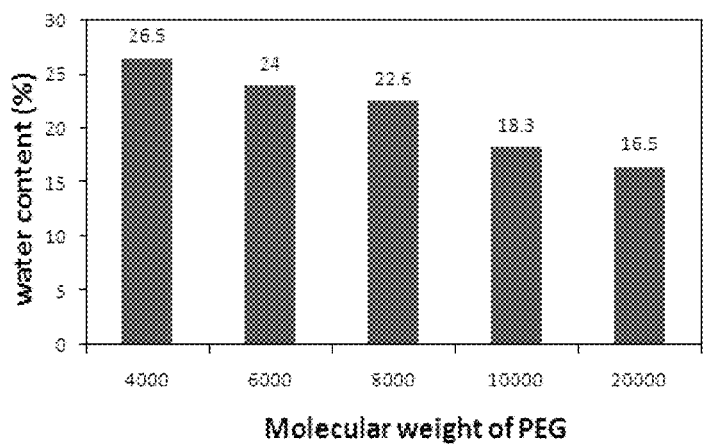
Figure 5C:
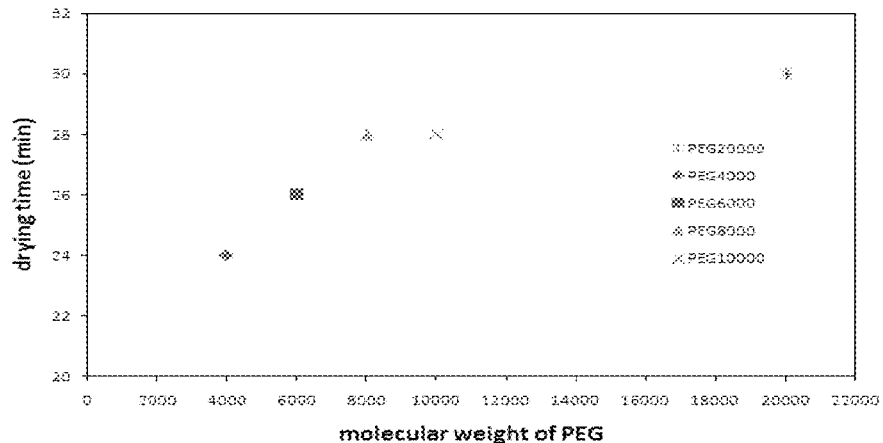
Figure 8C:
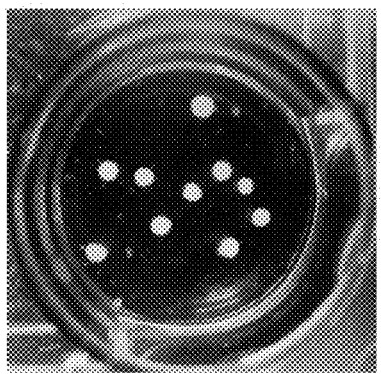
Figure 8D:
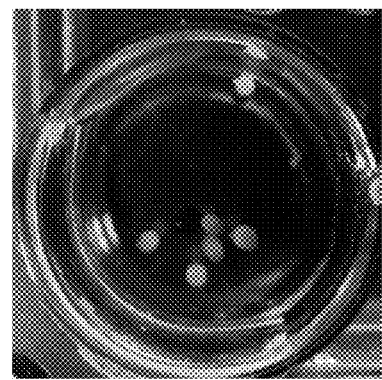

Using the apparatus setup of Example 3 (FIG. 4), the two immiscible phases are taken as polyethylene glycol (PEG) solution, which has the same osmolality but with a different molecular weight, for the external phase and an aqueous solution of starch (10% wt.) for the internal phase. Compared to Example 3, the second immiscible phase uses injector 43, capillary 42 and a second electrode 41. To control the particle size and water content and the entire processing time, the test is repeated with the two immiscible phases taken as polyethylene glycol (PEG) which has the same osmolality, but with a variety of different molecular weights for the external phase and an aqueous solution of starch (10% wt.) for the internal phase. It was found that by changing the molecular weight of PEG in the external phase, the size and water content of the starch particles and the processing time can be tuned and controlled. The effect of the change in molecular weight on volume, water content and drying time is illustrated in FIGS. 5(a)-5(c).

Example 5

Chronic myeloid leukemia cells are mixed in the internal starch phase to encapsulate them in the particles. Proper methods are taken to test the cell viability inside the solidified particles. Optical microscope images of the encapsulated cells released from the solidified particles are shown in FIG. 6, wherein FIG. 6(a) illustrates dead cells stained blue; FIG. 6(b) illustrates live cells not stained; and FIG. 6(c) illustrates live cells after encapsulation and subsequent release. This illustrates the biocompatibility of the present invention.

Besides soluble starch, an aqueous solution of dextran, chitosan, CMS-Na (Carboxyl Methyl Starch Sodium), corn starch and hydroxyethyl starch can be used as the droplet phase of the aqueous two phase emulsion system to fabricate solidified particles. FIGS. 7(a) and 7(b) are illustrations of solidified dextran particles in PEG solution and dextran particles on a glass slide that were formed according to the present invention. A dextran T500 solution (15 wt %) is used.

FIGS. 8(a) to 8(d) are illustrations of solidified chitosan particles in PEG solution, solidified CMS-Na particles in PEG solution, solidified corn starch particles in PEG solutions and solidified hydroxyethyl starch particles in PEG solution, respectively, formed according to the present invention. The Chitosan solution is 6 wt %, the CMS-Na solutions is 4 wt %, the corn starch solution is 10 wt % and the hydroxyethyl-starch solution is 10 wt %.

The present invention also works for the fabrication of solidified particles by treating emulsion droplets made by different methods. For example, a 3D microfluidic device can be used with the assistance of an external electric field to spray the internal phase into the external PEG phase drop-wise. As water is gradually extracted from the starch droplets, starch is solidified during the process. In the end, the solidified starch particles can be collected easily for further applications. Moreover, the PEG solution used as the concentrated solution can be recycled by techniques such as filtration and re-heating after the solidified particles have been taken out.

As illustrated by Example 5, the approach of the present invention for fabricating solidified particles has no harmful effects on the activity of the components that are encapsulated. Thus, the particles fabricated have a high preservation of bioactivity and cell viability.

The present invention is less intrusive to encapsulated ingredients, e.g., live cells can be encapsulated in starch particles using this solidification technique. The viability of cells encapsulated in this way is over 90%, which means this solidification technique has no negative effects on cells. This is much better than other solidification techniques. In particular, the viability of encapsulated cells formed by normal solidification technology, where the starch solution is mixed with cells and put in an oven at 37° C. to dry the solution, is just 10%. Other existing technologies like vacuum drying will kill cells because of the vacuum conditions.

The cost of the setup of the present invention is much lower than with other technologies. The cost comes from the fabrication of the injection device, with the purchase of filter screens and filtration papers. No large scale equipment is required.

For the large-scale deployment, the only thing needed is just to replace the one-tip microfluidic device with a multi-tip device. Such a device can be fabricated with Polydimethylsiloxane (PDMS) using 3D-printing. The cost of the fabrication process is low.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

While the invention has been particularly shown and described with reference to preferred embodiments thereof, it will be understood by those skilled in the art that various changes in form and details may be made therein without departing from the spirit and scope of the invention.

What we claim is:

1. A method for fabricating solidified particles from an all-aqueous emulsion system, comprising the steps of:
providing a continuous immiscible aqueous external phase of the emulsion; and
injecting a droplet of an immiscible aqueous internal phase of the emulsion, having a component dissolved therein, into the continuous external phase;
wherein the external phase has a high osmotic pressure gradient with respect to the internal phase such that water is extracted from the internal phase to the external phase, concentrating the components in the droplets of the aqueous internal phase to such an extent that solidification of the droplets into particles of the component is triggered.

2. The method of claim 1 wherein the component dissolved in the droplet of the immiscible aqueous internal phase of the emulsion is an inactive structural material that does not interact with aqueous external phase and further including the step of continuing the process until the droplet is solidified to form a particle of the structural material.

3. The method of claim 1 wherein the component dissolved in the droplet of the immiscible aqueous internal phase of the emulsion is an inactive structural material with an additional dissolved active ingredient and further including the step of continuing the process until the droplet is solidified to form a particle with the active ingredient encapsulated in a matrix of the structural material.

4. The method of claim 1 wherein the component dissolved in the droplet of the immiscible aqueous internal phase of the emulsion is an active structural material and further including the step of continuing the process until the droplet is solidified to form a particle of the active structural component.

5. The method of claim 3 wherein the inactive structural component is starch and the additional dissolved active component is an enzyme.

6. The method of claim 1 wherein the osmotic pressure gradient is controlled by the concentration of osmolytes in the external phase.

7. The method of claim 2 wherein the inactive structural component is starch and the external phase is an aqueous solution of polyethylene glycol (PEG).

8. The method of claim 7 wherein the starch has a weight average molecular weight MW=340 a concentration of about 10% wt. and the PEG has a MW=8000 and a concentration of about 40% wt.

9. The method of claim 1 wherein a change in the molecular weight of the external phase causes a change in the size and water content of the particles and the processing time.

10. The method of claim 3 wherein the active component in the droplet of the immiscible aqueous internal phase of the emulsion contains bioactive material, and further including the step of continuing the process until the droplet forms an encapsulated bioactive particle.

11. The method of claim 10 wherein the bioactive particle is one of the group of proteins, enzymes, DNA, RNA and cells, and there are no harmful effects on the bioactivity and cell viability of the bioactive particle.

12. The method of claim 3 wherein the active component is one of the group of proteins, enzymes, DNA, RNA and cells, and there are no harmful effects on the bioactivity and cell viability preserved, and the external phase is an aqueous solution of polyethylene glycol (PEG).

13. The method of claim 1 wherein the component is dextran and the external phase is an aqueous solution of polyethylene glycol (PEG).

14. The method of claim 13 wherein the internal phase is 15 wt % dextran T500 solution.

15. The method of claim 1 wherein the component is chitosan and the external phase is an aqueous solution of polyethylene glycol (PEG).

16. The method of claim 15 wherein the internal phase is 6 wt % chitosan solution.

17. The method of claim 1 wherein the component is CMS-Na and the external phase is an aqueous solution of polyethylene glycol (PEG).

18. The method of claim 7 wherein the starch is about 10 wt % hydroxyethyl starch.

* * * * *